United States Patent [19]
Puritch et al.

[11] Patent Number: 5,437,870
[45] Date of Patent: Aug. 1, 1995

[54] INGESTIBLE MOLLUSC POISONS

[75] Inventors: George S. Puritch, Saanichton; David S. Almond; Robert M. Matson, both of Victoria; Wenda M. Mason, Saanichton, all of Canada

[73] Assignee: W. Neudorff GmbH KG, Emmerthal, Germany

[21] Appl. No.: 295,606

[22] Filed: Aug. 25, 1994

[51] Int. Cl.⁶ .............................................. A02N 25/34
[52] U.S. Cl. .................................... 424/408; 424/84; 424/410; 424/404
[58] Field of Search .................. 424/404, 84, 410, 408; 514/492

[56] References Cited

U.S. PATENT DOCUMENTS

| | | | |
|---|---|---|---|
| 4,765,979 | 8/1988 | Nielsen | 424/84 |
| 4,983,390 | 1/1991 | Levy | 424/404 |
| 5,290,557 | 3/1994 | Mason et al. | 424/410 |
| 5,362,749 | 11/1994 | Henderson et al. | 514/492 |

FOREIGN PATENT DOCUMENTS 2207866A  2/1989  United Kingdom .

OTHER PUBLICATIONS

I. F. Henderson, et al., *Ann. Appl. Biol.* (1990), 116, 273–278.
I. F. Henderson, et al., *Crop Protection*, Apr. 1990, 9 131–134.
I. F. Henderson, et al., 1989 BCP Mono. No. 41 Slugs and Snails in World Agriculture 289–294.
Hendersen, et al., *Aspects of Appl. Biol.* (1986) 13, 341–347.

*Primary Examiner*—Thurman K. Page
*Assistant Examiner*—William E. Benston, Jr.
*Attorney, Agent, or Firm*—Lahive & Cockfield; William C. Geary, III

[57] ABSTRACT

An effective, readily ingested molluscicidal bait poison includes an inert mollusc bait and two active ingredient precursors. These precursors are edible and non-toxic to terrestrial molluscs when consumed alone. However, the composition which includes the two precursors is fatally toxic to terrestrial molluscs. One precursor is a simple iron compound, while the other precursor is selected from edetic acid, its hydroxyethyl derivatives and salts of these acids. In another embodiment a single active ingredient may replace the two precursors. This active ingredient may include ferric edetate and the ferric hydroxyethyl derivative of edetic acid.

10 Claims, No Drawings

INGESTIBLE MOLLUSC POISONS

BACKGROUND OF THE INVENTION

This invention relates to ingestible compositions for the control of terrestrial molluscs.

Terrestrial pulmonate gastropods, slugs and snails (collectively, molluscs) are significant plant pests that affect commercial agriculture and horticulture and domestic gardens. These molluscs are omnivorous and consume large amounts of vegetative materials during their daily foraging. Consequently, they can seriously damage vegetable gardens and even plant crops during all phases of the growing cycle. Because of their destructive potential, control measures must be employed to ensure adequate protection of the growing plants from damage by terrestrial molluscs.

A wide variety of approaches have been used to try to combat pest molluscs. Perhaps the most common is the use of poisonous compounds called molluscicides. Molluscicides include a diversity of chemical compounds such as table salt (NaCl), calcium arsenate, copper sulfate, and metaldehyde. Molluscicides fall into two major groups, depending upon their mode of action: contact poisons and ingestible (or bait) poisons.

Contact poisons are molluscicides that, to be effective, must come into physical contact with the exterior of the mollusc, either by external application or through the action of the mollusc traversing a molluscicidal composition placed on the ground. The contact molluscicide is picked up by the proteinaceous slime coat of the mollusc and it builds up in the body of the mollusc until a lethal proportion is reached. One of the major drawbacks of contact molluscicides is that they have little effect if the molluscs do not physically contact the active chemical agent. If the molluscs are hidden or migrate into an area after a contact molluscicide is spread, the molluscs are unaffected. For these reasons, contact-acting mollusc poisons generally are considered to be unreliable.

Heavy metals, including zinc, aluminum, copper and iron, are all toxic to molluscs and are examples of compounds known to be effective molluscicides when used as contact poisons in the form of salts or chelates. See, Henderson, et al. Crop Protection (1990), 9, 131-134 and Henderson, et al., Ann. Appl. Biol. (1990), 116, 273-278.

Ingestible (or bait) mollusc poisons are those that must be ingested by a mollusc in order to be lethal. This type of mollusc poison tends to be preferred over contact poisons only because contact poisons, which rely upon passive acquisition of the active ingredient, are not considered to be reliable. One challenge associated with the development of effective bait molluscicides is to prepare a composition that is both palatable to the mollusc and effective as a lethal poison. Obviously, a sufficient quantity of the poison must be ingested to reach the lethal threshold. Often, compositions that are palatable to the mollusc are not effective as a lethal poison, while compositions that are quite potent and lethal are not readily ingested by molluscs. Many contact poisons, such as aluminum sulfate, copper sulfate and borax, are useless as ingestible poisons because they are not palatable to molluscs, and the molluscs do not ingest a lethal dose of these compounds. Ingestible poisons must be sufficiently palatable to the mollusc so that they will be consumed in lethal amounts, but the composition must also be slow acting enough to prevent the mollusc from becoming sick or cause it to cease feeding.

Typical problems associated with the development of compounds for the effective control of molluscs are discussed by Henderson, et al. in Aspects of Appl. Biol. (1986) 13, 341-347. This publication recognizes that although many compounds are known to be poisonous to molluscs, there is considerable difficulty in delivering the poison to the mollusc either as a bait or as a contact poison. The potential toxicity of a compound is irrelevant if molluscs will not consume a lethal dose of a bait poison.

One of the few compounds that act as both a contact and bait poison for terrestrial molluscs is metaldehyde. This compound is commonly used as a long lasting bait, attracting the molluscs and killing them after they ingest the poison bait. Despite its high effectiveness and its commercial popularity, metaldehyde is toxic to higher mammals and is a major contributor to domestic animal poisoning in the U.S. and Europe. More recently, U.K. Patent Application 2 207 866A has reported that specific complexes of aluminum with pentanedione compounds and iron with nitroso compounds would act as both ingested and contact poisons.

There is thus a need to develop an effective ingestible poison for molluscs that is palatable to molluscs and that does not pose a threat to the environment, crops, animals and other non-pests.

Accordingly, it is an object of the invention to provide a toxic, ingestible composition that is palatable to terrestrial molluscs. Another object is provide such a composition that poses no significant threat to the environment, crops, animals, or other non-pests. Other objects will be apparent upon review of the following description.

SUMMARY OF THE INVENTION

The invention provides an effective ingestible poison that is lethal to terrestrial molluscs. The composition is comprised of constituent compounds which do not pose any significant threat to the environment, plants, animals and other non-pests. In one embodiment the composition combines an inert carrier, such as a bait, with a simple iron compound and a second component. The simple iron compound can be an iron protein, an iron carbohydrate or an iron salt. The second component may be edetic acid, or hydroxyethyl derivative of edetic acid or a salt of these acids. Individually, neither the simple iron compound nor the second component is toxic to terrestrial molluscs. It is believed that the composition becomes toxic to molluscs only after it is ingested by the molluscs. Preferably, the molar ratio of iron in the simple iron compounds to the second component is in the range of 1:0.2 to 1:2.0. Preferably, the iron component is present in an amount such that the concentration of iron within the composition is in the range of about 200 to 10,000 ppm.

In another embodiment the composition comprises a single active ingredient in combination with an inert ingredient such as a mollusc bait. The single active ingredient may be ferric edetate or a ferric hydroxyethyl derivative of edetic acid. Preferably, the active ingredient is present in an amount such that the concentration of iron within the composition is in the range of about 200 to 10,000 ppm.

DETAILED DESCRIPTION OF THE INVENTION

The present invention provides a bait poison that is effective against terrestrial molluscs. In one embodiment the composition of the invention combines an inert, edible mollusc bait with two active ingredient precursors. Individually the active ingredient precursors are not toxic to the molluscs. It is only when the entire composition, including the active ingredient precursors, is ingested by molluscs that molluscicidal activity is achieved.

One active ingredient precursor is a simple iron compound. The simple iron compound can be an iron protein, an iron carbohydrate or an iron salt. A second active ingredient precursor is selected from the group consisting of edetic acid a hydroxyethyl derivative of edetic acid, or salts of these acids.

In another embodiment the molluscicidal composition combines an inert, edible mollusc bait with an active ingredient such as ferric edetate or a ferric hydroxyethyl derivative of edetic acid.

An advantage of the molluscicidal composition of the present invention is that it exhibits good mortality against terrestrial molluscs and it is readily consumed by terrestrial molluscs. A further advantage of this composition is that the constituents of the composition are environmentally safe and pose no threat to humans, animals or other non-pests. In fact, with the exception of the iron salts of edetic acid or hydroxyethyl derivatives of edetic acid the individual components are non-toxic to molluscs when administered alone. The composition of the invention not only is lethal to molluscs, but molluscs are also poisoned to the extent that they cease feeding upon plants after consuming the composition.

Preferably, the molar ratio of iron in the simple iron compound to the second precursor ingredient is in the range of 1:0.2 to 1:2.0.

The simple iron compound can be selected from any one of a number of iron salt compounds including iron proteins, iron carbohydrates, and iron salts. The iron compound can be present in its iron (II) state (ferrous) as well as in its iron (III) state (ferric). Examples of suitable simple iron compounds are saccharated ferric oxide, ferric albuminate, ferric ammonium citrate, ferric chloride, ferric citrate, ferrous gluconate, ferrous lactate, ferric phosphate, ferrous phosphate, ferric pyrophosphate, ferric nitrate, ferrous sulfate, ferric stearate, ferrous stearate, and ferric tartrate. One characteristic of the simple iron compounds used as an active ingredient precursor in this invention is that they have little or no toxicity to the molluscs when used alone. Suitable simple iron compounds are commercially available from a variety of sources, including Dr. Paul Lohmann GmbH KG of Emmerthal, Germany.

The simple iron compound preferably is present within the composition at an amount such that the iron concentration in the composition is in the range of about 200 to 10,000 ppm. More preferably, the simple iron compound should be present in an amount such that the iron concentration in the composition is in the range of 2000 to 6000 ppm.

As noted above, the second active ingredient precursor can be edetic acid, hydroxyethyl derivative of edetic acid or salts of these acids. Preferred salts of these acids include the sodium salts, such as calcium disodium edetate, monosodium edetate, disodium edetate, trisodium edetate, tetrasodium edetate, calcium disodium hydroxyethylethylenediaminetriacetate, monosodium hydroxyethylethylenediaminetriacetate, and trisodium hydroxyethylethylenediaminetriacetate. The second active ingredient precursor preferably is present in the composition at a concentration in the range of about 2000 to 20,000 ppm More preferably this component is present at about 7,000 to 17,000 ppm.

In the embodiment of the invention in which the bait molluscicide includes a single active ingredient such as ferric edetate or the ferric hydroxyethyl derivative of edetic acid, this active ingredient preferably is present in a level such that the iron concentration is in the range of about 200 to 10,000 ppm.

The single active ingredients are available from a variety of commercial sources. One commercial source for ferric sodium edetate is Dr. Paul Lohmann GmbH KG of Emmerthal, Germany which sells ferric edetate (Lohmann ferric edetate). In addition, ferric edetate is commercially available from the Hampshire Chemical Unit of W. R. Grace & Co. of Lexington, Mass. under the mark Hamp-Ene ®. The hydroxyethyl derivative of ferric edetate is also available from the same unit of W. R. Grace under the marks Hamp-Ol ® and Hampshire ®.

The inert bait component of the molluscicidal composition of the invention is one that must be readily consumed by molluscs. A variety of mollusc baits are well known and may be used in the compositions of the present invention. Such baits include agar, potato dextrose agar, gelatin, oil cake, pet food, wheat, soya, oats, corn, rice, fruits, fish by-products, sugars, coated vegetable and cereal seeds, casein, blood meal, bone meal, yeast, fats, and a variety of cereals, including wheat cereal. A preferred bait is wheat cereal which is commercially available from various sources.

The molluscicidal bait composition of the invention may also include additional formulation enhancing additives. Such additives include preservatives or antimicrobial agents, phagostimulants, water-proofing agents, and taste altering additives.

A variety of preservatives can be used effectively with this molluscicidal bait composition. Examples of preferred preservatives include Legend MK ®, available from Rohm & Haas Company of Philadelphia, Pa. and CA-24, available from Dr. Lehmann and Co. of Memmingen/Allgäu, Germany. Preservatives such as these can normally be mixed with water to form a stock solution to be added to the formulation at a concentration in the range of about 10–750 ppm.

Phagostimulants can be added to the composition to attract molluscs and to induce molluscs to feed upon the composition. A variety of phagostimulants can be used, including sugars, yeast products and caesin. Sugars, such as sucrose, are among the more preferred phagostimulants. These additives are normally incorporated within the composition in a dry form. Typically, they can be added to the composition at about 1 to 2.5% by weight of the total composition.

Waterproofing agents, which can also act as binders, can be added to the composition to improve the weatherability of the molluscicidal bait. These are typically water insoluble compounds such as waxy materials and other hydrocarbons. Examples of suitable waterproofing agents are paraffin wax, stearate salts, beeswax, and similar compounds. One preferred wax compound is PAROWAX ®, available from Conros Corp. of Scarborough, Ontario, Canada. Waterproofing agents can be incorporated into the composition, in dry form, at about 5 to 12% by weight of the total composition.

It is also desirable to include within the molluscicidal bait taste altering compounds that render the composition unpalatable to animals. Exemplary compositions include those having a bitter taste. Suitable compounds that are commercially available include BITREX, available from Mcfarlane Smith Ltd. of Edinburgh, Scotland. These compounds typically are added at very low concentrations. For example, a 0.1% BITREX solution can typically be added to the composition at about 1 to 2% by weight of the total composition.

The molluscicidal bait of this invention typically is used in dry form and many of the constituent ingredients of the composition are included in dry form. However, it is useful to include a sufficient amount of water within the composition to form a dough so that the ingredients can be more easily formed. Water is typically added at about 15 to 60% by weight of the total composition. The water, however, typically is driven off by heating and drying the molluscicidal bait before it is used.

As noted above, the compositions of the present invention are typically used in a dry, spreadable form such as powders, granules, cubes, or pellets. The composition may be spread on or around areas infested by molluscs as well as in areas in which mollusc infestation is to be prevented.

Dry molluscicidal compositions according to the present invention can be prepared as follows.

A suitable amount of the active ingredient precursors, or the active ingredient, is blended, in dry form, with a dry mollusc bait, such as wheat flour. Thereafter, other dry ingredients (such as phagostimulants and waterproofing agents) are blended and mixed with the bait. Next, suitable amounts of liquid additives (such as preservatives, taste altering additives and water) are added to the dry mixture to form a dough. The bait can be covered, such as with plastic wrap, and heated. One preferred heating technique is by heating in a microwave oven for 30 seconds to 10 minutes. After heating, the dough can be processed in a food grinder to obtain strands of the bait material. This is then dried, at elevated or ambient temperatures, and can be made into a desired form, such as powder, pellets or granules.

An exemplary formulation of a suitable mollusc bait is as follows.

|  | INGREDIENT | PURPOSE | QUANTITY |
|---|---|---|---|
| DRY COMPONENTS | Wheat flour | Bait | 211.1 g |
|  | Edetic acid | a.i. Precursor | 2.7 g |
|  | Iron Compound | a.i. Precursor | 5.0 g |
|  | Paraffin Wax | Water-proofing | 25.0 g |
|  | Sucrose | Phagostimulant | 6.2 g |
| LIQUIDS | BITREX | Taste-altering | 5.0 g (0.1% sol'n) |
|  | Legend MK ® | Preservative | 33.3 g (0.015% sol'n) |
|  | Water | — | 67.1 g |
|  |  | TOTAL | 355.40 |

The barrier composition of the present invention is effective against a variety of terrestrial molluscs including Ariolimax spp.; Arion species including, Arion ater, A. hortensis, A. rufas, A. circumcriptus, A. empericorum; Deroceras spp.; Agriolimax spp.; Prophysaon spp.; Helix pomata; and Cepaea nemoralis.

The following examples serve to further illustrate the invention.

EXAMPLE 1

Molluscicidal baits were prepared according to the general procedure discussed above. The active ingredient precursors were added in sufficient amounts to yield the concentrations noted in Table 1A. The iron based active ingredient precursor used was saccharated ferric oxide (iron sugar). The following additional ingredients were also included in the mixture: 2.5% by weight sucrose and 20 ppm Legend MK ® antimicrobial agent, and 10% by weight paraffin wax. The control was prepared in a similar manner, except that it did not include the active ingredient precursors.

Tests were conducted in 25cm × 50cm × 5cm planting trays (two trays per treatment with 5 slugs per tray). Each tray was floored with wet potting soil and covered with a transparent, plastic lid. Each tray received five garden slugs, Arion ater. Ten grams of each of the formulations identified below in Table 1A were placed inside a petri dish and put in each planting tray along with a lettuce plant. The planting trays were placed outside in the shade during the course of the experiment. Table 1B illustrates the observed mortality (slugs killed/5) and percent of bait eaten for each formulation, at 6 days after testing (DAT).

TABLE 1A

| Tested Formulations | |
|---|---|
| Treatment | Formulation |
| 1A | 2000 ppm Fe from iron sugar |
| 1B | 2400 ppm Fe from iron sugar |
| 1C | 2800 ppm Fe from iron sugar |
| 1D | 3200 ppm Fe from iron sugar |
| 1E | 3200 ppm Fe from iron sugar + 16,400 ppm edetic acid |
| 1F | 10,400 ppm edetic acid |
| 1G | 12,400 ppm edetic acid |
| 1H | 14,400 ppm edetic acid |
| 1I | 16,400 ppm edetic acid |
| 1J | Control: Wheat flour, Paraffin wax, sucrose, 20 ppm Legend MK ® |

TABLE 1B

| Slug mortality (/5) and Bait Consumption (%) at 6 DAT | | |
|---|---|---|
| Treatment | Rep 1 | Rep 2 |
| A | 2000 ppm Fe | Spoiled | 0/5, 50% |
| B | 2400 ppm Fe | 0/5, 100% | 0/5, 70% |
| C | 2800 ppm Fe | 0/5, 80% | 0/5, 60% |
| D | 3200 ppm Fe | 0/5, 70% | 0/5, 40% |
| E | 3200 ppm Fe + 16,400 ppm edetic acid | 2/5, 20% | 3/5, 20% |
| F | 10,400 ppm edetic acid | 0/5, 30% | 0/5, 35% |
| G | 12,400 ppm edetic acid | 0/5, 30% | 0/5, 30% |
| H | 14,400 ppm edetic acid | 0/5, 20% | 0/5, 20% |
| I | 16,400 ppm edetic acid | 0/2, 15%* | 0/5, 15% |
| J | Control | Spoiled | 0/5, 70% |

*3 slugs missing

EXAMPLE 2

The formulations identified below in Table 2A were prepared by the general procedure noted above. The active ingredient precursors were used in sufficient amounts to yield the concentrations noted in Table 2A. The iron-based active ingredient precursor used was saccharated ferric oxide. Additional ingredients used in the formulations included 10% by weight paraffin wax, 2.5% by weight sucrose and 20 ppm Legend MK ®.

Test were conducted in 36 liter plastic tubs (two tubs per treatment with ten slugs per tub). Each tub was floored with wet potting soil and covered with a lid. Each tub received ten garden slugs, Arion ater. Ten grams of each molluscicidal bait identified in Table 2A was added to two petri dishes and placed in a tub along with two lettuce plants. The tubs were left outdoors during the course of the experiment.

The tubs were examined three days after treatment and seven days after treatment to assess the slug mortality (slugs killed/10) and amount of each molluscicidal bait eaten. These data are presented in tables 2B and 2C. Bait consumption is rated according to the following standards: heavy, greater than 20% bait consumed; moderate, 10 to 20% bait consumed; and light, less than 10% bait consumed.

TABLE 2A

Test Formulations

| Formulation | Component |
|---|---|
| 2A | 2800 ppm Fe from iron sugar + 14,400 ppm edetic acid |
| 2B | 2800 ppm Fe from iron sugar + 10,800 ppm edetic acid |
| 2C | 2800 ppm Fe from iron sugar + 7,200 ppm edetic acid |
| 2D | 2800 ppm Fe from iron sugar + 3,600 ppm edetic acid |
| 2E | 2800 ppm Fe from iron sugar |
| 2F | Control: Wheat flour, Parowax ®, sucrose, 20 ppm Legend MK ® |
| 2G | 2800 ppm Fe from ferric edetate (Lohmann) |

TABLE 2B

Slug mortality (/10) and Bait Consumption at 3 DAT

| Treatment | Rep 1 | Rep 2 |
|---|---|---|
| 2A  2800 ppm Fe from iron sugar + 14,400 ppm edetic acid | 0/9, 1 heavy* | 0/10, heavy |
| 2B  2800 ppm Fe from iron sugar + 10,800 ppm edetic acid | 0/10, moderate | 0/10, moderate |
| 2C  2800 ppm Fe from iron sugar + 7,200 ppm edetic acid | 0/10, moderate | 1/10, moderate |
| 2D  2800 ppm Fe from iron sugar + 3,600 ppm edetic acid | 0/10, heavy | 0/10, heavy |
| 2E  2800 ppm Fe from iron sugar | 0/10, heavy | 0/10, heavy |
| 2F  Control: Wheat flour, Parowax ®, sucrose, 20 ppm Legend MK ® | 0/10, heavy | 0/10, heavy |
| 2G  2800 ppm Fe from ferric edetate (Lohmann) | 0/10, moderate | 0/10, moderate |

*1 slug missing

TABLE 2C

Slug mortality (/10) at 7 DAT

| Treatment | Rep 1 | Rep 2 | Total |
|---|---|---|---|
| 2A  2800 ppm Fe from iron sugar + 14,400 ppm edetic acid | 6/9 | 5/10 | 11/19 |
| 2B  2800 ppm Fe from iron sugar + 10,800 ppm edetic acid | 7/10 | 6/10 | 13/20 |
| 2C  2800 ppm Fe from iron sugar + 7,200 ppm edetic acid | 7/10 | 5/10 | 12/20 |
| 2D  2800 ppm Fe from iron sugar + 3,600 ppm edetic acid | 2/10 | 5/10 | 7/20 |
| 2E  2800 ppm Fe from iron sugar | 0/10 | 0/10 | 0/20 |
| 2F  Control: Wheat flour, Parowax ®, sucrose, 20 ppm Legend MK ® | 0/10 | 0/10 | 0/20 |
| 2G  2800 ppm Fe from ferric edetate (Lohmann) | 5/10 | 5/10 | 10/20 |

EXAMPLE 3

Compounds identified below in Table 3A were prepared according to the general procedure noted above. The active ingredient precursors were added in sufficient quantities to yield the concentration noted in Table 3A. The following additional ingredients were also added for each formulation: 10% by weight of paraffin wax, 2.5% by weight sucrose and 20 ppm Legend MK ®.

Tests were conducted in 25 cm×50cm×5cm planting trays (two trays per treatment with 5 slugs per tray). Each tray was floored by wet potting soil and covered by transparent plastic lids. Each tray received 5 garden slugs, Arion ater, and ten grams of bait which was placed inside a petri dish and placed on the soil along with a lettuce plant. The trays were placed outside in the shade during the course of the experiment.

The slug mortality (slugs killed/5) and percent of bait consumed was evaluated at 6 DAT and these data are shown in Table 3B.

TABLE 3A

Tested Formulations

| Formulation | Components |
|---|---|
| 3A | 2000 ppm Fe from iron-III-phosphate |
| 3B | 2800 ppm Fe from iron-III-phosphate |
| 3C | 2000 ppm Fe from iron-III-citrate |
| 3D | 2800 ppm Fe from iron-III-citrate |
| 3E | 2000 ppm Fe from iron-III-pyrophosphate |
| 3F | 2800 ppm Fe from iron-III-pyrophosphate |
| 3G | 2000 ppm Fe from iron-III-nitrate |
| 3H | 2800 ppm Fe from iron-III-nitrate |
| 3I | 2000 ppm Fe from iron-III-sugar |
| 3J | 2800 ppm Fe from iron-III-sugar |
| 3K | Control: Wheat flour, Parowax ®, sucrose, 20 ppm Legend MK ® |

TABLE 3B

Slug Mortality (/5) and Bait Consumption (%) at 6 DAT

| Formulation | Rep 1 | Rep 2 |
|---|---|---|
| 3A  2000 ppm Fe from iron-III-phosphate | 0/5, 30% | 0/5, 20% |
| 3B  2800 ppm Fe from iron-III-phosphate | 0/4*, 15% | 0/5, 30% |
| 3C  2000 ppm Fe from iron-III-citrate | 0/5, 30% | 0/5, 30% |
| 3D  2800 ppm Fe from iron-III-citrate | 0/5, 20% | 0/5, 20% |
| 3E  2000 ppm Fe from iron-III-pyrophosphate | 0/5, 90% | 0/5, 60% |
| 3F  2800 ppm Fe from iron-III-pyrophosphate | 0/2, 15%* | 0/5, 40% |
| 3G  2000 ppm Fe from iron-III-nitrate | 0/5, 60% | 0/5, 60% |
| 3H  2800 ppm Fe from iron-III-nitrate | 0/5, 40% | 0/5, 15% |
| 3I  2000 ppm Fe from iron-III-sugar | 0/5, 70% | 0/5, 35% |
| 3J  2800 ppm Fe from iron-III-sugar | 0/5, 50% | 0/5, 80% |
| 3K  Control: Wheat flour, Parowax ®, | 0/5, 40% | 0/5, 60% |

TABLE 3B-continued

| Slug Mortality (/5) and Bait Consumption (%) at 6 DAT | | |
|---|---|---|
| Formulation | Rep 1 | Rep 2 |
| sucrose, 20 ppm Legend MK ® | | |

*1 slug missing
**2 slugs missing

EXAMPLE 4

The formulations identified in Table 4A were prepared according to the general procedure noted above. The active ingredient precursors were added in sufficient amounts to yield the concentration shown in Table 4A. Additional ingredients for each formulation included 10% by weight paraffin wax, 2.5% by weight sucrose, and 20 ppm Legend MK ®.

Tests were conducted in 36 liter plastic tubs (2 tubs per treatment with 10 slugs per tub). Each tub was floored by wet potting soil and covered with a plastic lid. Each tub received 10 garden slugs, Arion ater, and ten grams of bait, which was placed inside a petri dish. The petri dishes were placed on the soil along with two lettuce plants. The tubs were left outside during the course of the experiment. The tubs were examined at 1 DAT and 6 DAT to determine slug mortality (slugs killed/10) and the percent of the bait consumed. These data are illustrated below in Tables 4B and 4C.

TABLE 4A

| Treatment Formulations | |
|---|---|
| Formulation | Components |
| 4A | 2800 ppm Fe from iron phosphate |
| 4B | 2800 ppm Fe from iron phosphate + 10,800 ppm edetic acid |
| 4C | 2800 ppm Fe from iron lactate |
| 4D | 2800 ppm Fe from iron lactate + 10,800 ppm edetic acid |
| 4E | 10,800 ppm edetic acid |
| 4F | Control: Wheat flour, paraffin wax, sucrose, 20 ppm Legend MK ® |

TABLE 4B

| Slug mortality (/10) and Bait Consumption % at 1 DAT | | |
|---|---|---|
| Treatment | Rep 1 | Rep 2 |
| 4A 2800 ppm iron phosphate | 0/10, 35% | 0/10, 25% |
| 4B 2800 ppm iron phosphate + edetic acid | 0/10, 20% | 0/10, 20% |
| 4C 2800 ppm iron lactate | 0/10, 20% | 0/10, 30% |
| 4D 2800 ppm iron lactate & edetic acid | 0/10, 25% | 0/10, 20% |
| 4E 10,800 ppm edetic acid | 0/10, 30% | 0/10, 15% |
| 4F Control | 0/10, 40% | 0/10, 85% |

TABLE 4C

| Slug mortality (/10) and Bait Consumption (%) at 6 DAT | | |
|---|---|---|
| Treatment | Rep 1 | Rep 2 |
| 4A 2800 ppm iron phosphate | 0/10, 60% | 0/10, 100% |
| 4B 2800 ppm iron phosphate & edetic acid | 7/10, 40% | 8/10, 30% |
| 4C 2800 ppm iron lactate | 0/10, 70% | 0/10, 60% |
| 4D 2800 ppm iron lactate + edetic acid | 7/10, 40% | 5/10, 30% |
| 4E 10,800 ppm edetic acid | 0/10, 85% | 0/10, 70% |
| 4F Control | 0/10, 100% | 0/10, 100% |

EXAMPLE 5

The bait compositions identified in Table 5A were prepared according to the general procedure noted above. Active ingredient precursors were added in sufficient amounts to yield the concentrations noted. Additional ingredients included 10% paraffin wax, 2.5% by weight sucrose and 20 ppm Legend MK ®.

The tests were conducted using 36 liter plastic tubs (2 tubs per treatment with 10 slugs per tub). Each tub was floored by wet potting soil and covered with a plastic lid. Each tub received 10 garden slugs, Arion ater, and ten grams of bait which was placed inside a petri dish and placed on the soil in each tub along with two lettuce plants. The tubs were left outside during the course of the experiment.

The tubs were examined at 1 DAT and 6 DAT to determine the slug mortality (slugs killed/10) and the amount of bait consumed. These data are illustrated in Tables 5B and 5C.

TABLE 5A

| Test Formulations | |
|---|---|
| Formulation | Components |
| 5A | 2800 ppm Fe from iron pyrophosphate |
| 5B | 2800 ppm Fe from iron pyrophosphate + 10,800 ppm edetic acid |
| 5C | 2800 ppm Fe from iron nitrate |
| 5D | 2800 ppm Fe from iron nitrate + 10,800 ppm edetic acid |
| 5E | 10,800 ppm edetic acid |
| 5F | Control: Wheat flour, paraffin wax, sucrose, 20 ppm Legend MK ® |

TABLE 5B

| Slug Mortality (/10) and Bait Consumed (%) at 1 DAT | | |
|---|---|---|
| Treatment | Rep 1 | Rep 2 |
| 5A 2800 ppm iron pyrophosphate | 0/10, 50% | 0/10, 40% |
| 5B 2800 ppm iron pyrophosphate + edetic acid | 0/10, 15% | 0/10, 25% |
| 5C 2800 ppm iron nitrate | 0/11, 20% | 0/10, 20% |
| 5D 2800 ppm iron nitrate + edetic acid | 0/10, 30% | 0/10, 20% |
| 5E 10,800 ppm edetic acid | 0/10, 25% | 0/10, 30% |
| 5F Control | 0/10, 40% | 0/10, 60% |

TABLE 5C

| Slug mortality (/10) and Bait Consumption (%) at 6 DAT | | |
|---|---|---|
| Treatment | Rep 1 | Rep 2 |
| 5A 2800 ppm iron pyrophosphate | 0/10, 80% | 0/10, 90% |
| 5B 2800 ppm iron pyrophosphate + edetic acid | 8/10, 20% | 4/10, 30% |
| 5C 2800 ppm iron nitrate | 0/10, 70% | 0/10, 80% |
| 5D 2800 ppm iron nitrate + edetic acid | 1/10, 30% | 3/10, 20% |
| 5E 10,800 ppm edetic acid | 0/10, 50% | 0/10, 50% |
| 5F Control | 0/10, 100% | 0/10, 100% |

EXAMPLE 6

The bait compositions identified in Table 6A were prepared according to the general procedure noted above. Active ingredient precursors were added in sufficient amounts to yield the concentrations noted. Additional ingredients included 10% by weight paraffin wax; 2.5% by weight sucrose; and 20 ppm Legend MK ®.

Feeding tests were conducted inside 36 liter plastic containers. Two containers were used for each treatment so that there were two replicates. Each container was filled to 3 cm with potting soil that was made damp. Ten slugs, Arion ater, were placed into each tub at the start of the experiment. At the same time, 10 grams of bait was placed into a petri dish and the dish was placed on the soil in the container. Two lettuce plants or one potted marigold plant were placed on their side and positioned on the soil within the container as an alternate food source. The containers were then covered with plastic lids and the tubs were placed outside in a shaded area. The containers were evaluated at 5 DAT and 6 DAT by counting all living and dead slugs and removing the dead slugs. At the same time, the plants and the bait were examined to determine the amount of bait consumed. Table 6B, below, illustrates the slug mortality and the bait consumption for replicates 1 and 2 at 5 DAT. Table 6C illustrates the total slug mortality for the two replicates.

TABLE 6A

Test Formulations

| Formulation | Components |
|---|---|
| 6A | 2800 ppm Fe from iron ammonium citrate |
| 6B | 2800 ppm Fe from iron ammonium citrate plus 10,800 ppm edetic acid |
| 6C | 2800 Fe from iron chloride |
| 6D | 2800 ppm Fe as iron chloride plus 10,800 ppm edetic acid |
| 6E | 2.00% f Fe edetate (2800 ppm Fe) |
| 6F | Control: Wheat, wax, Legend MK ® |

TABLE 6B

Slug Mortality and Bait Consumption (%) at 5 DAT.

| Treatment | Rep 1 | Rep 2 |
|---|---|---|
| 6A 2800 iron ammonium citrate | 2/10, 90% | 0/10, 70% |
| 6B 2800 iron ammonium citrate plus edetic acid | 8/10, 40% | 7/10, 30% |
| 6C 2800 iron chloride | 0/10, 50% | 0/8, +2, 80% |
| 6D 2800 ppm iron chloride plus edetic acid | 5/10, 30% | 4/10, 30% |
| 6E 10,800 edetic acid | 0/10, 40% | 0/10, 60% b |
| 6F Control | 0/10, 90% | 0/10, 100% |

+two slugs missing

TABLE 6C

Total Slug Mortality at 6 DAT.

| Treatment | Rep 1 | Rep 2 | Total |
|---|---|---|---|
| 6A 2800 ppm iron ammonium citrate | 2/10 | 0/10 | 2/20 |
| 6B 2800 ppm iron ammonium citrate plus edetic acid | 9/10 | 7/10 | 16/20 |
| 6C 2800 ppm iron chloride | 0/10 | 0/8 | 0/18 |
| 6D 2800 ppm iron chloride plus edetic acid | 9/10 | 5/10 | 14/20 |
| 6E 10,800 ppm edetic acid | 0/10 | 0/10 | 0/20 |
| 6F Control | 0/10 | 0/10 | 0/20 |

EXAMPLE 7

The formulations shown in Table 7A were prepared according to the general procedure noted above. The tests were conducted using ½ liter food containers (2 containers per treatment with 3 slugs per container). Each container was floored by wet potting soil and covered with transparent, plastic lids. Each container received 3 garden slugs, Deroceras reticulatum, and a cube of bait placed directly on the soil. The containers were examined at 1 DAT and 5 DAT to determine the slug mortality and the bait consumption. Bait consumption was recorded according to a scale in which "heavy" indicates greater than 20 percent bait consumption; "moderate" indicates 10 to 20 percent consumption; and "light" indicates less than 10 percent bait consumption. The data obtained are illustrated in Tables 7B and 7C below.

TABLE 7A

Test Formulations

| Formulation Code | Components |
|---|---|
| 7A | Control: wheat flour, paraffin wax, sucrose, 20 ppm Legend MK ® |
| 7B | 2232 ppm Fe from iron sugar + 16,400 ppm sodium edetate |
| 7C | 2232 ppm Fe from iron chloride + 16,400 ppm sodium edetate |

TABLE 7B

Slug Mortality and Bait Consumption at 1 DAT

| Treatment | Rep 1 | Rep 2 |
|---|---|---|
| 7A Control | 0/3, heavy | 0/3, heavy |
| 7B 2232 ppm Fe from sugar + sodium edetate | 0/3, moderate | 0/3, light |
| 7C 2232 ppm Fe from iron chloride + sodium edetate | 0/3, light | 0/3, light |

TABLE 7C

Slug Mortality and Bait Consumption at 5 DAT

| Treatment | Rep 1 | Rep 2 |
|---|---|---|
| 7A Control | 0/2*, heavy | 0/3, heavy |
| 7B 2232 ppm Fe from sugar + sodium edetate | 2/2* moderate | 2/3, light |
| 7C 2232 ppm Fe from iron chloride + sodium edetate | 0/3, light | 1/3, light |

*1 slug missing

EXAMPLE 8

The baits identified in Table 8A were prepared according to the general procedure noted above. Hamp-Ene ® ferric sodium edetate was obtained from W. R. Grace and Company of Lexington, Mass. and Lohmann ferric sodium edetate was obtained from Dr. Paul Lohmann GmbH KG of Emmerthal, Germany. Tests were conducted in 36 liter tubs (2 tubs per treatment with 10 Deroceras reticulatum per tub). Each tub had a soil covering the base of the tub and the tub was covered with a plastic lid. Three lettuce plants were placed in the tubs as an alternate feeding source. Slugs were introduced to the tubs at the time the baits were added.

The tubs were examined at 4 DAT to determine slug mortality. These data are shown in Table 8B.

TABLE 8A

Test Formulations

| Formulation Code | Components |
|---|---|
| 8A | 2800 ppm Fe from Ferric edetate (Hamp-Ene ®) + 750 ppm CA-24 |
| 8B | 2800 ppm Fe from Ferric edetate + 750 ppm CA-24 |
| 8C | Control: Wheat flour, paraffin wax, sucrose, 20 ppm Legend MK ® or Ca-24 |
| 8D | 2800 ppm Fe from ferric edetate (Hamp-Ene ®) |

TABLE 8B

Slug mortality at 4 DAT.

| Treatment | Rep 1 | Rep 2 |
|---|---|---|
| 8A 2800 ppm Fe from Ferric edetate (Hamp-Ene ®) + 750 ppm CA-24 | 6/10 | 4/10 |
| 8B 2800 ppm Fe from Ferric edetate + 750 ppm CA-24 | 7/10 | 4/9* |
| 8C Control: Wheat flour, paraffin wax, sucrose, 20 ppm Legend MK ® or Ca-24 | 0/10 | 0/8** |
| 8D 2800 ppm Fe from ferric edetate | 9/10 | 10/10 |

TABLE 8B-continued

| | Slug mortality at 4 DAT. | |
|---|---|---|
| Treatment | Rep 1 | Rep 2 |
| (Hamp-Ene ®) | | |

*1 slug missing
**2 slugs missing

One of ordinary skill in the art will appreciate that minor modifications may be made to the compositions of the present invention without departing from its intended scope.

What is claimed is:

1. A terrestrial mollusc stomach poison composition, comprising
    a simple iron compound selected from the group consisting of iron proteins, iron carbohydrates, and iron salts, which, alone, have little or no toxicity to the molluscs;
    a second component selected from the group consisting of edetic acid, hydroxyethyl derivative of edetic acid, or salts thereof; and
    an inert carrier material edible to molluscs, wherein the molar ratio of the iron in the simple iron compound to the second component is in the range of 1:0.2 to 1:2.0.

2. The composition of claim 1 wherein the simple iron compound is present in an amount such that the iron concentration within the composition is in the range of about 200–10,000 ppm.

3. The composition of claim 1 wherein the second component is present at a concentration in the range of 2000 to 20,000 ppm 4. The composition of claim 1 wherein the simple iron compound is present in an amount such that the iron concentration within the composition is in the range of about 2000 to 6,000 ppm and the second component is present at a concentration of about 7,000 to 17,000 ppm.

5. The composition of claim 1 wherein the second component, in its salt form, is selected from the group consisting of calcium disodium edetate, monosodium edetate, disodium edetate, trisodium edetate, tetrasodium edetate, calcium disodium hydroxyethylethylenediaminetriacetate, monosodium hydroxyethylethylenediaminetriacetate and trisodium hydroxyethylethylenediaminetriacetate.

6. The composition of claim 1 wherein the simple iron compound is selected from the group consisting of saccharated ferric oxide, ferric albuminate, ferric ammonium citrate, ferric chloride, ferric citrate, ferrous gluconate, ferrous lactate, ferric phosphate, ferrous phosphate, ferric pyrophosphate, ferric nitrate, ferrous sulfate, iron stearate, and ferric tartrate.

7. The composition of claim 1 wherein the inert carrier is selected from the group consisting of wheat cereal, agar, gelatin, oil cake, pet food wheat, soya, oats, corn, rice, fruits, fish by-products, sugars, coated vegetable and cereal seeds, casein, blood meal, bone meal, yeast, and fats.

8. A terrestrial mollusc stomach poison composition, comprising:
    an effective amount of an active ingredient selected from the group consisting of ferric edetate and a ferric hydroxyethyl derivative of edetic acid.

9. The composition of claim 8 wherein the active ingredient is present in an amount such that the iron concentration is in the range of about 200–10,000 ppm.

10. The composition of claim 8 wherein the inert carrier is selected from the group consisting of wheat cereal, agar, gelatin, oil cake, pet food wheat, soya, oats, corn, rice, fruits, fish by-products, sugars, coated vegetable and cereal seeds, casein, blood meal, bone meal, yeast, and fats.

* * * * *

UNITED STATES PATENT AND TRADEMARK OFFICE
CERTIFICATE OF CORRECTION

PATENT NO. : 5,437,870
DATED : August 1, 1995
INVENTOR(S) : George S. Puritch, David S. Almond, Robert M. Matson and Wenda M. Mason It is certified that error appears in the above-indentified patent and that said Letters Patent is hereby corrected as shown below:

Claim 8, line 5, please change "." to --; and--

Claim 8, after line 5, please add

--an inert carrier material edible to molluscs.--

Signed and Sealed this

Seventh Day of October, 1997

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,437,870
DATED : August 1, 1995
INVENTOR(S) : George S. Puritch et al.

It is certified that error appears in the above-indentified patent and that said Letters Patent is hereby corrected as shown below:

In the Specification:

|  | Reads | Should Read |
|---|---|---|
| Col. 14, line 20 (Claim 7) | pet food wheat | pet food, wheat |
| Col. 14, line 34 (Claim 10) | pet food wheat | pet food, wheat |

Signed and Sealed this

Fourth Day of April, 2000

Attest:

Q. TODD DICKINSON

*Attesting Officer*          *Director of Patents and Trademarks*